(12) United States Patent
Kun et al.

(10) Patent No.: US 6,316,495 B1
(45) Date of Patent: Nov. 13, 2001

(54) METHOD FOR INHIBITION OF RETROVIRAL REPLICATION

(75) Inventors: Ernest Kun, Mill Valley; Kalman G. Buki, San Francisco, both of CA (US)

(73) Assignee: Octamer, Inc., Berkeley, CA (US)

( * ) Notice: Subject to any disclaimer, the term of this patent is extended or adjusted under 35 U.S.C. 154(b) by 0 days.

(21) Appl. No.: 09/227,392

(22) Filed: Jan. 8, 1999

Related U.S. Application Data

(63) Continuation of application No. 08/155,087, filed on Nov. 19, 1993, now abandoned, which is a continuation of application No. 07/936,067, filed on Aug. 26, 1992, now abandoned, which is a continuation of application No. 07/683,607, filed on Apr. 10, 1991, now abandoned.

(51) Int. Cl.$^7$ .................................................. A61K 31/35
(52) U.S. Cl. .......................................... 514/456; 514/457
(58) Field of Search ..................................... 514/456, 457

(56) References Cited

FOREIGN PATENT DOCUMENTS

WO 89/07939 * 8/1989 (WO) ............................ A61K/31/37

OTHER PUBLICATIONS

Hakam et al, FEBS Letters, vol. 212, No. 1, pp. 73–78 Feb. 1987.*

Tseng et al, Proc. Natl. Acad. Sci. USA, vol. 84, pp. 1107–1111 Feb. 1987.*

* cited by examiner

*Primary Examiner*—Russell Travers
(74) *Attorney, Agent, or Firm*—Albert P. Halluin; Viola T. Kung; Howrey Simon Arnold & White, LLP

(57) ABSTRACT

A method for inhibition of retroviral replication by manipulation of enzyme adenosine diphosphoribosyl transferase which endogenously inhibits retroviral reverse transcriptase. The method is useful for prevention and treatment of retroviral infections, including HIV. The inhibition of the viral replication is achieved by administration to a mammal susceptible to or infected with a retrovirus drugs which specifically inhibit poly-ADP-ribosylation of adenosine diphosphoribosyl transferase.

7 Claims, 3 Drawing Sheets

METHOD FOR INHIBITION OF RETROVIRAL REPLICATION

This application is a continuation of U.S. application Ser. No. 08/155,087, filed Nov. 19, 1993, now abandoned; which is a continuation of U.S. application Ser. No. 07/936,067, filed Aug. 26, 1992, now abandoned; which is a continuation of U.S. application Ser. No. 07/683,607, filed Apr. 10, 1991, now abandoned.

BACKGROUND OF THE INVENTION

1. Field of Invention

This invention concerns a method for inhibition of a retroviral replication by inhibition of poly-ADP-ribosylation of the enzyme adenosine diphosphoribosyl transferase which, in nonribosylated state endogenously inhibits retroviral reverse transcriptase. In particular, this invention concerns a prevention of retroviral replication, including replication of the HIV, by administering to a mammal susceptible to or infected with retrovirus or with HIV, drugs which specifically inhibit poly-ADP-ribosylation of ADPRT and thereby activation of retroviral reverse transcriptase.

2. Related Disclosures

Retroviruses, particularly such retroviruses as human immunodeficiency virus, visna virus of sheep, equine infections anemia virus, ovine visna maldi, caprin arthritis-encephalitic virus, feline infectious peritonitis and feline immunodeficiency virus have many similar morphological, biological and molecular characteristics. Biologically, these viruses cause slowly progressive, fatal disease in their mammalian host.

Retroviruses contain an enzyme called reverse transcriptase used for the synthesis of a DNA molecule within the host cell using retroviral, RNA as a template. Reverse transcriptase is coded for by the pol gene in the respective viral genomes. Reverse transcriptase is incorporated into the infectious viral particles so that it is available and able to act immediately when the infecting particle enters an appropriate host cell. Reverse transcriptase can copy viral RNA in the host cell cytoplasm into DNA, which may replicate from extrachromosomal sites or move into the cell nucleus where it becomes part of the host cell DNA. These integrated viral genes duplicate synchronously with normal cellular genes, and all progeny of the originally infected cells will contain the viral genes.

Expression of the viral genes for some retroviruses may be either infectious, causing the viral infections such as those named above, it may be oncogenic, converting the normal cells into cancerous cells, or it may have other pathologic effects which may alter normal cell function or produce cell death.

The essential feature of the retroviral, including HIV, infection is the viral replication. The process of viral replication consists of several steps of which each represents a potential target for therapeutic intervention.

The initial step of the retroviral infection is the binding of the virion particle to the target cell, generally a lymphocyte or macrophage. Viral binding involves the interaction of a free viral particle with the surface of a target cell. After binding of the virus to the target cell surface, the infecting virus must be internalized. This is accomplished by the interaction of the viral sequences with the cell membrane. The result of this interaction is the fusion of the viral envelope with the cell membrane.

Once internalized, the viral RNA genome undergoes reverse transcription and subsequent integration into the host genome. Recent data derived from the study of murine leukemia viruses, described in *J. Clin. Invest.* 73:191 (1984), suggest that these enzymatic processes occur in the context of a subviral particle consisting of a nucleoprotein complex that can be found both in the cytoplasm and nucleus. Reverse transcription, catalyzed by the virally encoded reverse transcriptase, involves the synthesis of first-strand DNA and the second strand DNA, which is complementary of the first strand. The integration of retroviral DNA into the host chromosomal DNA is dependent on a virally encoded endonuclease which seems to utilize the linear double-stranded DNA provirus as its substrate. The retroviral integration process exhibits features characteristic of transposition such as the generation of a duplication of host DNA sequences at the site of integration.

After integration, the DNA provirus will be intensely transcribed to generate many progeny virion RNAs and spliced subgenomic messenger RNAs (mRNAs). Thus, the regulation of retroviral transcription is complex and involves the interaction of various cellular factors.

Although HIV exhibits certain unique morphological features, its virion, a complete mature viral particle, has a structure similar to that of other retroviruses and behaves essentially in the same way. In most respects, HIV infection resembles that of other retroviruses. However, a very important feature of HIV infection exhibited by relatively few other retroviruses is that productive infection of the target CD4$^+$ cells results in dramatic cytopathic effects including syncytia formation and cell death. One of the unusual features of HIV infection, as compared with that of most other retroviruses, is the accumulation of large amounts of unintegrated DNA and DNA termini, which accumulation has been found in only few other retroviral systems.

It would thus be extremely important to be able to prevent the replication of the viral RNA genome by inhibition of reverse transcription. Any delay of the reverse transcription increases the probability of degradation of viral RNA genome by host cell RNAase enzymes.

Molecular approaches to prevention and therapy of retroviral and HIV infections are not new. The primary goal of these approaches is the inhibition of intracellular replication of retrovirus or HIV. The inhibition of synthesis of viral DNA by reverse transcriptase inhibitors such as dideoxy-nucleosides or specific antibodies has been described for example in *Immunol. Today*, 8:1 (1987).

The 2,3-dideoxynucleosides appear to be taken up by T lymphocytes and to undergo phosphorylation to generate 2,3-dideoxynucleoside 5' triphosphates. These analogues can be utilized directly by reverse transcriptase and incorporated into an elongating DNA chain; however, the absence of a 3' OH group on the sugar moiety prevents the formation of the subsequent 5'-3' phosphodiester bond, resulting in premature chain termination. Retroviral reverse transcriptases appear to be more sensitive to dideoxynucleoside-induced chain termination than do host cell DNA polymerases, thus resulting in the therapeutic usefulness of these compounds. Two particular dideoxynucleosides that have shown clinical promise are 3'-azido, 3'-deoxythymidine (AZT) and 2,3-dideoxycytidine. These compounds can induce long-term inhibition of HIV replication in vitro. Of the two, although very toxic AZT is now widely used in AIDS patients after the clear demonstration of its efficacy in prolonging life span in certain groups of AIDS and ARC patients.

With the success of these antiviral agents, it can be anticipated that many new inhibitors of reverse transcriptase will soon be evaluated for their therapeutic usefulness in AIDS. Interestingly, the presence of antibodies that inhibit reverse transcriptase catalytic activity has been correlated with improved clinical status, provide yet another therapeutic approach. Present concepts, relating also to viral chemotherapy are reviewed by De Clercq in "New Acquisitions in the Development of Anti-HIV Agents", *Antiviral Res.*, 12: 1–20 (1989).

The current invention concerns the inhibition of reverse transcriptase by the host cell nuclear protein adenosine-diphosphoribosyl transferase (ADPRT) present in eucaryotes which, by binding to a reverse transcriptase template, i.e. to the viral genome, can inhibit viral reverse transcription.

Recently, certain compounds were shown to specifically bind to ADPRT at the same site that also binds catalytically effective DNA termini. It is evident that such compounds and DNA compete for the same site on ADPRT. These results, disclosed in *FEBS Lett.*, 212:73 (1987), also describe the biological role of ADPRT was described extensively. With the aid of synthetic ligands of ADPRT, these drug were shown to inhibit DNA proliferation, particularly in tumorigenic cells.

Currently, certain drugs having a potent antiviral activity were discovered, to which are able to inhibit the activation mechanism for reverse transcriptase, present in the host cell.

SUMMARY

One aspect of the current invention is the prevention of a retroviral replication by the inhibition of the reverse transcriptase by an endogenously present inhibitor adenosine diphosphoribosyl transferase.

Another aspect of the current invention is the prevention of a human immunodeficiency virus replication by the inhibition of the reverse transcriptase by an endogenously present inhibitor adenosine diphosphoribosyl transferase.

Another aspect of the current invention is the inhibition of the viral replication wherein said inhibition is achieved by inhibition of the auto-ADP-ribosylation Aof the adenosine diphosphoribosyl transferase caused by damaged DNA.

Another aspect of the current invention is the inhibition of the viral replication wherein said inhibition is achieved by binding of the adenosine diphosphoribosyl transferase to the reverse transcriptase template in the presence of drugs which abrogate the reverse transcriptase activation by oligomers of adenosine diphosphoribosyl covalently bound to adenosine diphosphoribosyl transferase by auto-ADP-ribosylation.

Still another aspect of the current invention is the inhibition of the viral replication by 6-amino-1,2-benzopyrones, 5-iodo-6-amino-1,2-benzopyrones, coumarines, isoquinolines or quinizarines, wherein said inhibition is due to the inhibition of the poly-ADP-ribosylated adenosine diphosphoribosyl transferase which activates reverse transcriptase.

DETAILED DESCRIPTION OF THE INVENTION

Figure 1:
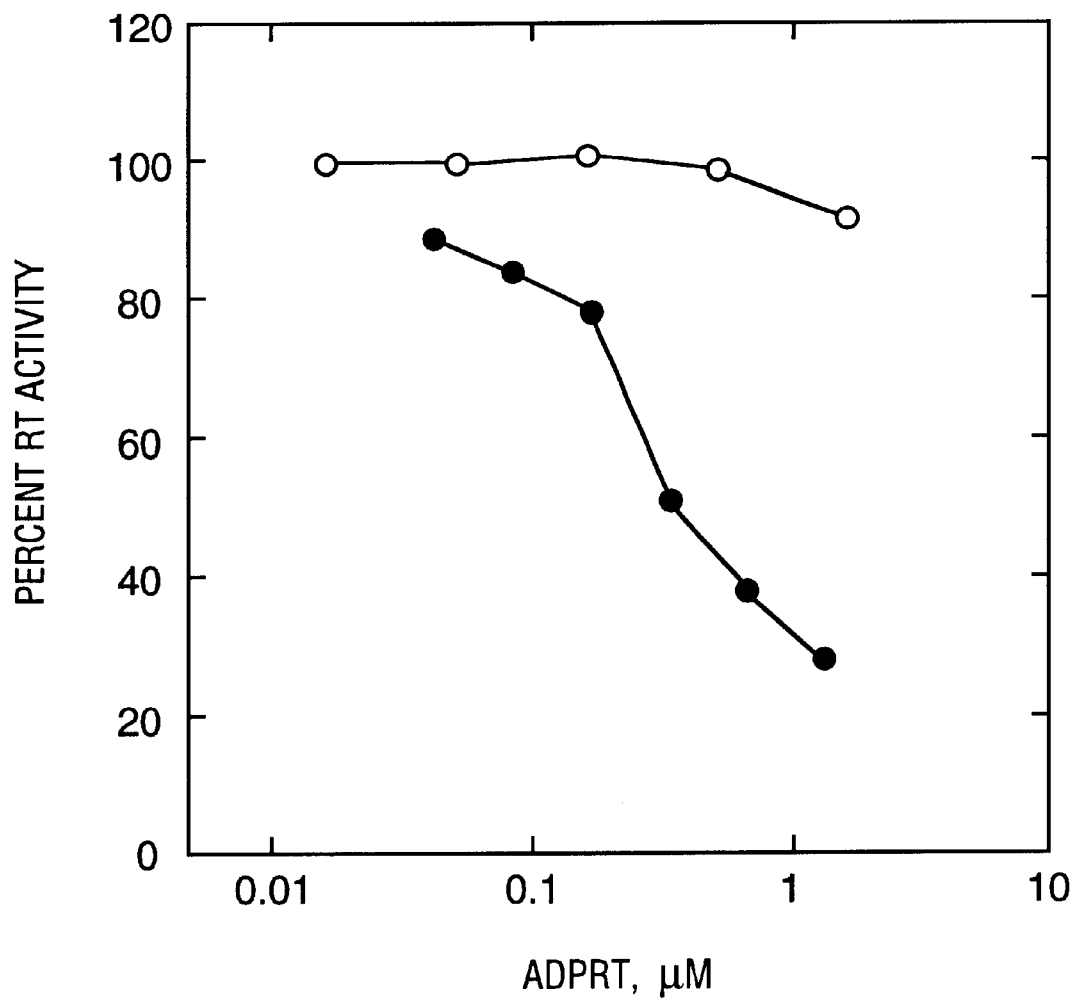
FIG. 1 shows the effect of ADPRT on human immunodeficiency virus reverse transcriptase activity.

In retroviral infection propagation of DNA of the virus formed by viral reverse transcriptase, a viral replication is a critical step.

It has been now found that the viral replication may be advantageously manipulated by certain non-toxic drugs acting on the molecular level. This invention concerns the enzyme ADPRT present in the cells which acts as an endogenous inhibitor of the invading virus reverse transcriptase in healthy host cells containing intact unbroken DNA. Thus, when the healthy cell is subjected to viral infection, its own ADPRT enzyme inhibits the reverse transcriptase of the invading virus. This results in inability of the virus to replicate within the host cell and in effect it prevents a spread of viral infection.

When, however, the host cells DNA is damaged in any way, as for example, by the radiation, drug abuse, chemical injury, infection or some such other stimulus, the reverse transcriptase of the invading virus is activated. According to the findings of the invention, this activation of reverse transcriptase seems to be caused by the auto-ADPRT-ribosylation of the ADPRT enzyme. Such auto-ADP-ribosylation of the ADPRT enzyme occurs spontaneously in the host cells when the broken DNA termini and/or fragments are present. The auto-ADP-ribosylation of ADPRT results from the polymerization derived from NAD ever present in an abundant amount in the cells. In the presence of broken DNA, the ADPRT enzyme catalyzes the polymerase reaction forming polymer poly-ADP-ribose $(ADPR)_{n>x}$ oligomer, wherein a number (X) designates the number of ADPR units incorporated by the polymerization. It has been found that when the n is larger than 9 and particularly when it is larger than 30, the activation of reverse transcriptase increases.

The $(ADPR)_{n>9}$ oligomers bind covalently to ADPRT, forming an $ADPRT/(ADPR)_{n>9}$ complex. The $(ADPR)_{n>9}$ oligomer somehow inhibits the ADPRT's reverse transcriptase inhibitory activity and in this way it acts as a potent activator of the viral reverse transcriptase.

In effect, the broken or damaged DNA causes ADPRT to be auto-modified by said polymer formation to such an extent that its normal protective function against invading virus is reversibly abolished. The involved enzymatic reaction in in vivo and in the presence of broken DNA, proceeding in direction of polymerization. Since the ADPRT/$(ADPR)_{n>9}$ complex may be hydrolyzed by low activity enzyme hydrolase, the polymerization reaction is ultimately reversible. In vitro, the polymerization reaction is irreversible.

The current invention which concerns the inhibition of the process of reverse transcriptase activation, as described above, is thus based on three major findings, namely that the nuclear protein of eucaryotes ADPRT (ADP-ribose transferase, E.C.2.4.2.30) is a protein which, by binding to the reverse transcriptase template, inhibits viral reverse transcriptase that this inhibition is abrogated by as short as (n>9) oligomers of adenosine diphosphoribosyl (ADPR) covalently bound to ADPRT by auto-ADP-ribosylation in the absence of DNA fragments; and that the poly ADP-ribosylated ADPRT (auto-ADP-ribosylation performed in the presence of fragmented DNA) is a powerful activator of viral reverse transcriptase, indicating that ADPRT (ADPR)$_{n>9}$ complex is a significant cellular component of the HIV reverse transcriptase system operating in the cells of HIV-infected patients suffering from active AIDS.

The retroviral infection propagation via retrovirus replication by viral reverse transcriptase was studied in vitro using a process catalyzed by highly purified recombinant reverse transcriptase obtained from human HIV.

Reverse transcriptase activity in vitro requires dTTP (deoxythymidine triphosphate) as substrate and a template consisting of poly (rA) with a sedimentation velocity of 10.7S annealed to oligo (dT)$_{n=12-18}$. In the in vitro system, the radioactive substrate was used and its incorporation in a time-dependent manner was measured.

In the mammal cells, viral reverse transcription performs the same catalytic function, except that certain complications are known to obscure the picture so clearly seen in vitro studies. For example, in HIV infected cells (humans), the infection tends to remain latent for unpredictable periods, and viral activation (i.e., onset of the disease) is elicited by toxic factors (drug abuse) or coviral infections (i.e., HSV) and by other ill-defined factors. Complicating this picture is the long-suspected contribution of host-cell factors required for the activation and maintenance of reverse transcriptase activity.

Two sets of studies were performed to determine whether in fact the ADPRT enzyme acts as reverse transcriptase inhibitor and whether such inhibition is prevented when ADPRT is modified by the (ADPR)$_n$ polymer, in another words, whether the viral reverse transcriptase is activated with ADPR residues covalently bound to ADPRT by auto-ADP-ribosylation. The results are shown in FIGS. 1 and 2.

Figure 2:
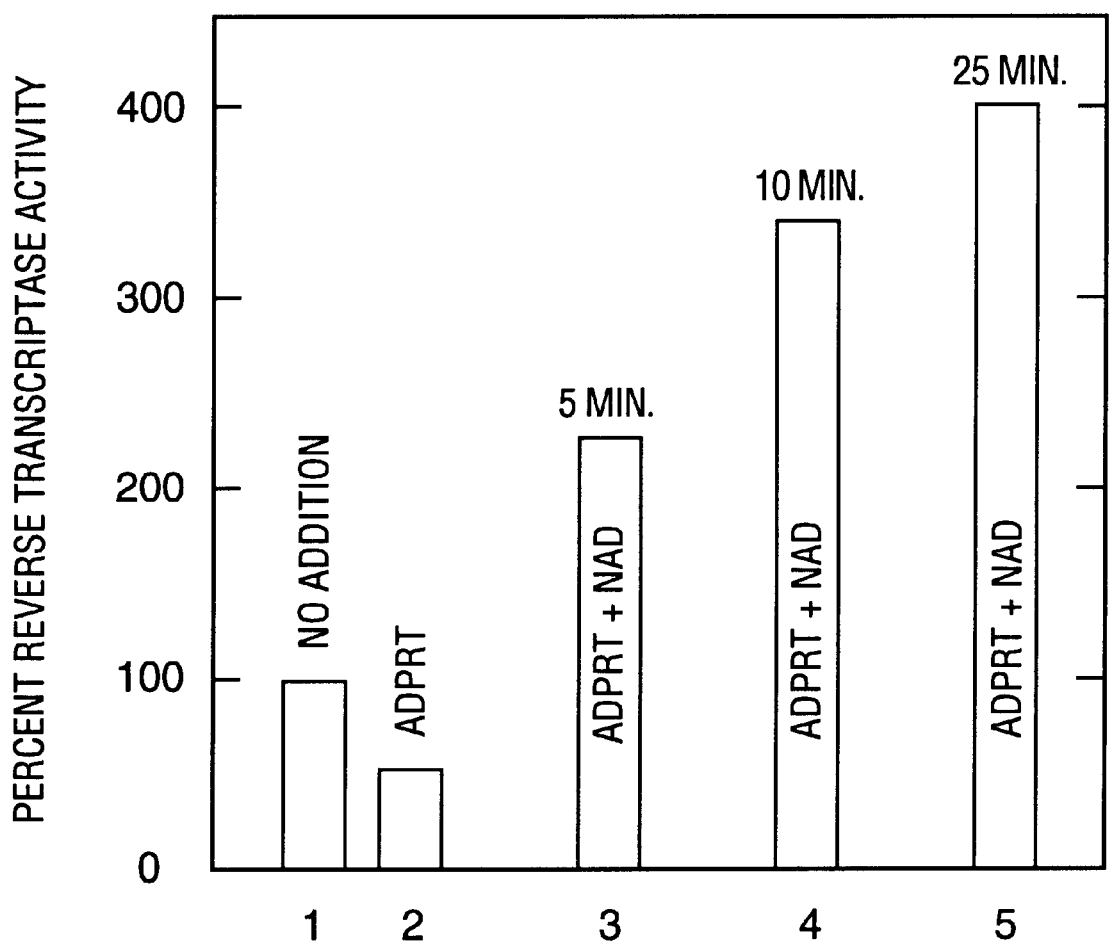
FIG. 2 shows the activation of reverse transcriptase by auto-(ADP-ribosylated) ADPRT.

FIG. 1 illustrates the effect of pure unmodified ADPRT on HIV reverse transcriptase activity as compared to the effect of poly-ribosylated ADPRT/ADPR$_{n=35}$ on the NIH reverse transcriptase.

The basic assay system for measurement of reverse transcriptase activity is described in Example 1. Human recombinant HIV reverse transcriptase used in the assay was obtained from HIV, ERC Bioservices. ADPRT used in this experiment is highly purified ADPRT protein prepared according to Anal. Biochem., 167:160 (1987). ADPRT was added to the reverse transcriptase assay system at various concentrations ranging from 0.01 to 1 $\mu$M. When the effect of pure, i.e., pre-ADP-ribosylated ADPRT was assayed, the ADPRT enzyme was incubated with NAD and cofactors according to FEBS Letters, 212:73 (1987). The poly ADP-ribosylated ADPRT was isolated by centricon ultrafiltration and added in various concentration as shown in FIG. 1.

FIG. 1 illustrates the inhibitory effect of pure ADPRT protein on human reverse transcriptase. The lower curve (-•-•-) shows the inhibitory effect of unmodified ADPRT, ordinate expressing % reverse transcriptase activity. Since the endogenous cellular concentration ADPRT is around 1–1.3 $\mu$M, the obtained results reflect the actual cellular conditions.

The top curve (-•-•-•-) shows the loss of inhibitory action. In this case, ADPRT contained an average of 35 ADPR molecules covalently bound to 1 mol of ADPRT forming ADP-ribosylated ADPRT.

As seen from the -•-•- curve, the pure unmodified ADPRT is able to inhibit the HIV reverse transcriptase substantially. Starting with 100% activity of control reverse transcriptase, the addition of 0.05 $\mu$M of pure ADPRT was able to inhibit 10% of the reverse transcriptase activity. With increasing amount of the pure ADPRT, the inhibition of reverse transcriptase was progressively increased until at around 1–1.3 $\mu$M of ADPRT which, as pointed out above, is the endogenous concentration of ADPRT present in the cells, the inhibition was around 75–80%, i.e., the activity of reverse transcriptase was only about 20%.

As seen from the upper -•-•-•- curve, the inhibitory effect of pure ADPRT, as seen in the lower curve (-•-•-), was lost almost completely when the ADPRT was ADP-ribosylated (-•-•-•-), regardless of what the concentration of ADPRT/ADPR$_{n=35}$ complex was. Up to about 0.9 $\mu$M of ADPRT/ADPR$_{n=35}$ complex, the activity of reverse transcriptase was sustained at round 100%. Only the slight decrease in reverse transcriptase activity was observed when the concentration of the complex dropped to about 1 $\mu$M.

Results seen in FIG. 1 show that in in vitro conditions simulating normal cellular conditions, unmodified, i.e., endogenous-like ADPRT prevents viral reverse transcription. The viral transcription is thus almost completely inhibited in the presence of ADPRT and the HIV infection is kept latent due to the inhibition of replication.

When, however, ADPRT is ADP-ribosylated and becomes the ADPRT/ADPR$_{n>9}$ complex, such ADP-ribosylated ADPRT activates the reverse transcriptase, exerting thus its own inhibitory effect on reverse transcriptase inhibition of native endogenous ADPRT. Since it is well known that such poly-ADP-ribosylation occurs spontaneously when the DNA is in a damaged or broken form, it is self-evident that under such circumstances, the inhibitory effect of ADPRT on reverse transcriptase is removed and the HIV replication proceeds, resulting in the massive HIV infection. Thus, the prior ADP-ribosylation of ADPRT abrogates the inhibition of reverse transcriptase by nonmodified ADPRT.

Such abrogation and its time dependency is further illustrated in FIG. 2 wherein the activation of HIV reverse transcriptase by auto-ADP-ribosylated ADPRT is expressed as % of reverse transcriptase activity. The experimental conditions are as described in Example 3. Column 1 shows the control 100% of reverse transcriptase activity in an incubation mix containing a medium as described in Example 1, the reverse transcriptase activity in the presence of 0.5 $\mu$M of ADPRT (columns 2–5); or in the presence of ADPRT and 62.5 $\mu$M of NAD (Columns 3–5), and containing 0.05 units of recombinant human HIV reverse transcriptase and a template consisting of poly (rA) oligo(dT)$_{12-18}$. Samples in columns 3–5 were incubated for time periods as indicated.

As seen from FIG. 2, the presence of pure ADPRT, under these experimental conditions, depressed/inhibited reverse transcriptase activity by about 50%. In the presence of NAD and ADPRT, not only that inhibitory effect, was abrogated but the reverse transcriptase was powerfully activated depending on the time of incubation. The longer the time of incubation, the larger the activation. Thus, the poly-ADP-ribosylation ADPRT acted instead as a powerful activator of viral reverse transcriptase.

Since the similar conditions as those simulated in experiments of FIG. 2, exist in normal cells, this study shows that in the absence of the broken DNA in the cells, ADPRT is able to inhibit almost completely the reverse transcriptase activity and thus prevent the viral replication and the spread of the viral infection. In the presence of the broken or damaged DNA termini or fragments which act as a template, the poly ADP-ribosylation of ADPRT proceeds with time and is able to activate the reverse transcriptase. Since all components needed for such activation, i.e., NAD, ADPRT, and the template are present in the host cell when the virus invades the host cells and since the reverse transcriptase is provided by the virus itself, the activation of the viral reverse transcriptase proceeds rapidly, resulting in rapid viral replication and in the spread of infection.

Figure 3:
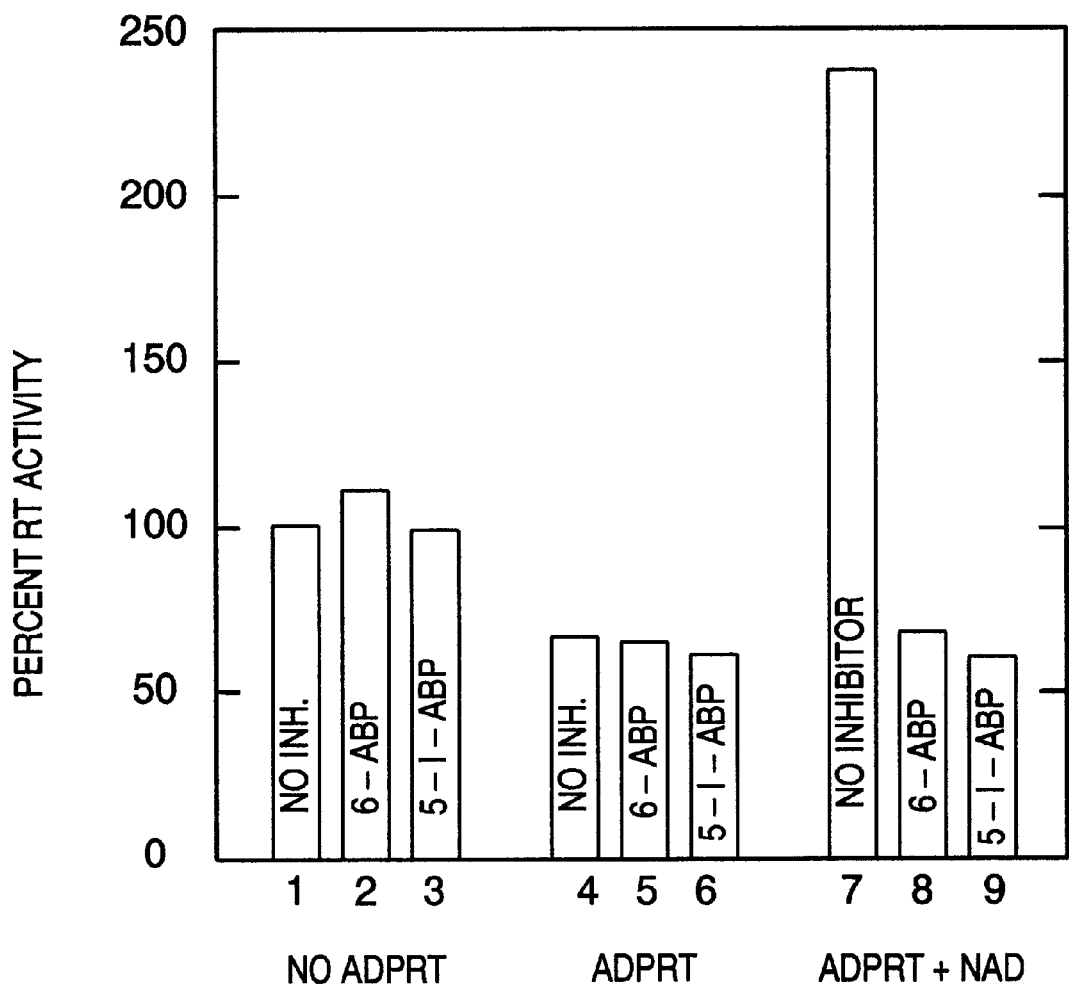
FIG. 3 shows HIV reverse transcriptase activity in the presence of ADPRT, poly-ADP-ribosylated ADPRT and drug inhibitors of poly-ADP-ribosylation of ADPRT.

Certain groups of drugs, including those disclosed and described in copending patent applications Ser. No. 585,231, filed on Sep. 21, 1990, incorporated hereby by reference in its entirety, and Ser. No. 600,593, filed on Oct. 19, 1990, incorporated hereby by reference in its entirety, such 6-amino-1,2-benzopyrones or 5-iodo-6-amino-1,2- benzopyrones were discovered to inhibit the reverse transcriptase even in the presence of a template simulating broken or damaged DNA. The results of these studies are illustrated in FIG. 3. Other drugs, such as coumarines, described in *Proc. Natl. Acad. Sci.*, 84:1107 (1987), or isoquinolines, described in *Tetrahedron*, 37:3977 (1981), or quinizarines, described in *Am. Chem. Soc.*, 48:420 (1926), are similarly active.

FIG. 3 shows the HIV reverse transcriptase activity in the presence (columns 4–6) or absence (columns 1–3) of ADPRT or in combination of ADPRT and NAD, the presence of which, as seen above, promotes the poly-ADP-ribosylation of ADPRT (columns 7–9). Reverse transcriptase activity assay conditions were as described in Example 1. NAD was added in a concentration of 62.5 μM and ADPRT in a concentration of 0.5 μM. Inhibitors 6-amino-1,2-benzopyrone (6-ABP) or 5-iodo-6-amino-1,2-benzopyrone (5-I-6-ABP) were added in concentrations 1000 μM, and 400 μM, respectively. When inhibitors 6-ABP or 5-I-6-ABP were added to these three groups according to described experimental conditions, the results show that in the absence of the ADPRT enzyme (columns 1–3), the presence of 6-ABP inhibitor (column 2) or 5-I-6-ABP inhibitor (column 3) did not affect the activity of the HIV reverse transcriptase and that such activity was the same or similar as in the control sample (column 1) which contained no ADPRT and no drug inhibitor.

When the exactly the same experiment was done in the presence of ADPRT, however, as seen in columns 4–5, the activity of reverse transcriptase as seen in column 4, containing only the pure native ADPRT, and columns 5 and 6, containing drug inhibitors 6-ABP or 5-I-ABP, columns 5 and 6 respectively, the activity of reverse transcriptase was inhibited to about 50%, regardless whether the sample contained only ADPRT or ADPRT and the drug inhibitor.

Thus, the effect of 6-ABP or 5-I-6-ABP, in the presence of pure ADPRT decreases the reverse transcriptase only very slightly.

In the third group (columns 7–9), where the samples contained poly-ADP-ribosylated ADPRT without presence of the drug inhibitor (column 7), the activity of reverse transcriptase reached around 240% of activity. When under the same circumstances, the drug 6-ABP at a concentration of 1000 μM was added (column 8), the reverse transcriptase activity was decreased to about 60%, that is to the same level as seen in column 5 Similarly, when 5-I-6-ABP was added at a concentration of 400 μM (column 9) to the sample containing HIV reverse transcriptase, where the ADPRT is ADP-ribosylated, the activity of reverse transcriptase was also the same as the one seen in column 6, where the drug inhibitor acted in the presence of pure ADPRT. These new drug inhibitors are thus as potent inhibitors of reverse transcriptase as is the pure native ADPRT enzyme, but exert their inhibitory action by inhibition of ADP-ribosylation of ADPRT.

UTILITY

This invention concerns the prevention of viral replication of potent retroviruses such as human immunodeficiency virus or other sush as cyto-megalovirus, herpes simplex viruses or lentiviruses such as visna virus of sheep, equine infections anemia virus, ovine visna maldi, caprin arthritis-encephalitic virus, feline infectious peritonitis and feline immunodeficiency virus. These viruses are very infectious and cause severe diseases which are often fatal to the host organism. The prevention of viral replication by the method of this invention is achieved by selective inhibition or blockade of the poly-ADP-ribosylation of the ADPRT enzyme.

The prevention of the viral replication by the method of this invention differs from other known methods for viral replication in that it acts on the ADPRT (ADPR)$_n$ complex of the host cells and not on the reverse transcriptase of the invading virus. Thus, the method of the current invention acts as or promotes the autodefense mechanisms of the host cells.

This, of course, is extremely important finding because, in this way, the cells of the host organism may be primed before the infection by invading virus will happen.

Since the compounds which were found to inhibit poly-ABP-ribosylation of the ADPRT enzyme are largely very little or not at all toxic, they can be administered preventively to the risk groups of individuals, such as to the gay population, drug users, individuals undergoing radiation or chemotherapy or suffering from hereditary genetic disease, and to the other groups which are susceptible to the serious viral infections.

The method will be equally useful for prevention and treatment of all high mammals, including humans.

The active compounds known to have the ability to inhibit poly-ADP-ribosylation of ADPRT belong to the group of compound generally called 6-amino-benzopyrones (6-ABP) of the formula

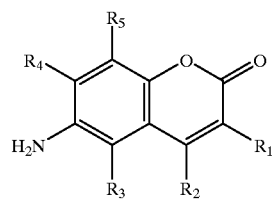

wherein $R_1$, $R_2$, $R_3$, $R_4$ or $R_5$ are each independently selected from hydrogen, hydroxy, amino, alkyl, alkox, cycloalkyl, phenyl or substituted phenyl with alkyl, alkoxy, hydroxy, or halo, or their pharmaceutically active and acceptable salts;

or the group of compounds generally called 5-iodo-6-aminobenzopyrones (5-I-6-ABP) of the formula

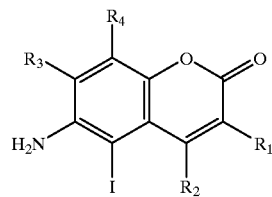

wherein $R_1$, $R_2$, $R_3$, or $R_4$, are each independently selected from hydrogen, hydroxy, amino, alkyl, alkoxy, cycloalkyl, halo, phenyl or substituted phenyl with alkyl, alkoxy, hydroxy, or halo, or their pharmaceutically active and acceptable salts;

or the group of compounds generally called coumarines of the formula

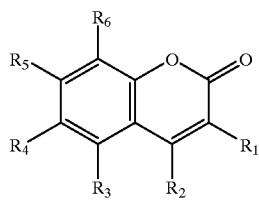

wherein $R_1$, $R_2$, $R_3$, $R_4$, $R_5$, $R_6$, or $R_7$ are each independently selected from hydrogen, hydroxy, amino, alkyl, alkoxy, cycloalkyl, halo, phenyl or substituted phenyl with alkyl, alkoxy, hydroxy, or halo, or their pharmaceutically active and acceptable salts;

or the group of compounds generally called isoguinolines of the formula

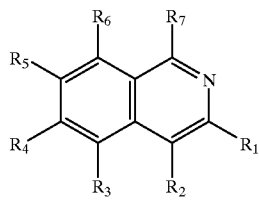

wherein $R_1$, $R_2$, $R_3$, $R_4$, $R_5$ or $R_6$, $R_7$ are each independently selected from hydrogen, hydroxy, amino, alkyl, alkoxy, cycloalkyl, halo, phenyl or substituted phenyl with alkyl, alkoxy, hydroxy, or halo, or their pharmaceutically active and acceptable salts;

or the group of compounds generally called guinizarines of the formula

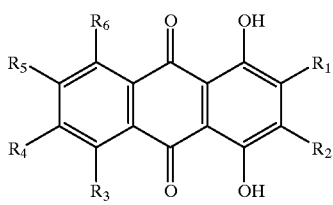

wherein $R_1$, $R_2$, $R_3$, $R_4$, $R_5$ or $R_6$ are each independently selected from hydrogen, hydroxy, amino, alkyl, alkoxy, cycloalkyl, halo, phenyl or substituted phenyl with alkyl, alkoxy, hydroxy, or halo, or their pharmaceutically active and acceptable salts.

These compounds, or their pharmaceutically acceptable salts would be formulated in any manner suitable and customary in pharmaceutical sciences, such as for example any parenteral or oral formulation.

Administration of the active compounds and salts described herein can be via any of the accepted modes of administration for therapeutic agents. These methods include systemic or local administration such as oral, parenteral, transdermal, subcutaneous, or topical administration modes. The preferred method of administration of these drugs is intravenous, except in those cases where the subject has topical lesions, such as HSV lesions and sores, where the topical administration may be proper. In other instances, it may be necessary to administer the composition in other parenteral or even oral. forms.

Depending on the intended mode, the compositions may be in the solid, semi-solid or liquid dosage form, such as, for example, injectables, tablets, suppositories, pills, time-release capsules, powders, liquids, suspensions, or the like, preferably in unit dosages. The compositions will include an active compound chosen from those listed above or the pharmaceutically acceptable salt thereof, and in addition, it may include any conventional pharmaceutical excipients and other medicinal or pharmaceutical agents, carriers, adjuvants, diluents, etc.

The amount of active compound administered will, of course, be dependent on the subject being treated, on the subject's weight, the severity of the affliction, the manner of administration and the judgment of the prescribing physician. However, an effective dosage is in the range of 0.01 to 5000 mg/kg/day, preferably 0.1 to 1000 mg/kg/day, more preferably 1 to 100 mg/kg/day. The upper limit of course is when the patient shows toxic effects. However, since the compounds of this invention are practically non-toxic, the administered dose may be as high as needed.

For solid compositions, in addition to the active compound such excipients as for example, pharmaceutical grades of mannitol, lactose, starch, magnesium stearate, sodium saccharin, talcum, cellulose, glucose, sucrose, magnesium carbonate, and the like may be used. The active compound, as defined above, may be also formulated as suppositories using, polyalkylene glycols, for example, propylene glycol, as the carrier.

Liquid, particularly injectable compositions can, for example, be prepared by dissolving, dispersing, etc. an active compound in a pharmaceutical solution such as, for example, water, saline, aqueous dextrose, glycerol, ethanol, and the like, to thereby form the injectable solution or suspension.

Parenteral injectable administration is generally used for subcutaneous, intramuscular or intravenous injections and infusions. Injectables can be prepared in conventional forms, either as liquid solutions or suspensions or, solid forms suitable for dissolving in liquid prior to injection.

A more recently devised approach for parenteral administration employs the implantation of a slow-release or sustained-released systems, which assures that a constant level of dosage is maintained. See, e.g., U.S. Pat. No. 3,710,795, which is incorporated herein by reference.

Normally, active compound would not be effective per os because of the rapid detoxification of some of the active compounds or their derivatives in the liver, however, appropriate chemical modification of these compounds together with a simultaneous administration of glutathion depressing drug which would prevent such rapid metabolism in the liver is contemplated to be developed and is, as all other possible pharmaceutical compositions, within the scope of this invention.

If desired, the pharmaceutical composition to be administered may also contain minor amounts of nontoxic auxiliary substances such as wetting or emulsifying agents, pH buffering agents, and the other substances such as for example, sodium acetate, triethanolamine oleate, etc.

Actual methods of preparing such dosage forms are known, or will be apparent to those skilled in this art, and are in detail described in *Remington's Pharmaceutical Sciences*, Mack Publishing Company, Easton, Pa. 17th Edition, 1985. The composition or formulation to be administered will, in any event, contain such quantity of the active compound(s) which will assure that a therapeutically effective amount will be delivered to a patient. The therapeutically effective amount means an amount effective to prevent the development of or to alleviate the existing symptoms of the subject being treated.

In AIDS patients about 1 g of active compound/average body weight typically provides effective chemotherapy. The chemotherapy may be repeated intermittently while HIV is or even when it is not detectable.

Moreover, due to their low toxicity, the therapy may be provided alone or in combination with other antiviral or other drugs, such as for example AZT, antibiotics, corticosteroids, vitamins and other drugs. There are no contraindications for use of active compounds with AZT, or other drugs since modes of action are quite different and possible synergism between active compounds and other drugs is predictable.

Active compounds according to this invention are equally useful for treatment of herpetic lesions caused by both HSV-1 and HSV-2. The drug would be preferably administered by i.v. infusion or other parenteral or systemic mode of administration. In case of sores, the drug could be also administered topically. Infection caused by CMV would be treated preferably in the same fashion as that suggested for AIDS treatment.

The active compound/drug would be administered to the patient who is in a risk group, i.e., who is susceptible or who already contracted viral disease in an amount which would be pharmacologically effective for treatment and prevention of the viral infection by inhibiting poly-ADP-ribosylation of ADPRT.

This invention, including the mechanism of action of these drugs represent a new chemotherapeutic approach which acts in the same or similar manner as the native ADPRT enzyme and are thus useful for prevention of viral replication, particularly in individuals which are susceptible to or contracted viral infection or have their DNA damaged by collateral infections, radiations, cancer, drug abuse, hereditary DNA damage or for any other reasons.

It is within the scope of this invention that in the practice of the current invention, the patient who is susceptible to the retroviral infection, including HIV, or who already contracted the infection or disease would be treated with any compound known now or discovered later to be able to inhibit auto-poly-ADP-ribosylation of the ADPRT enzyme.

EXAMPLE 1

Reverse Transcriptase Assay

This example illustrates the reverse transcriptase assay conditions used.

The medium (coctail) comprises 50 mM Tris-HCl pH 8.0; 60 mM KCl; 7 mM $MgCl_2$; 40 mM DTT (dithiothreitol) 2 mM GSH (glutathione); 60 µg/ml whole histones/ml (Grade A, Sigma, St. Louis); poly (rA) oligo $(dT)_{12-18}$ (Pharmacia, Piscataway, N. J.) and 50 µM M(0.1 µCalif.) [alfa $^{32}$P]TTP (ICN, Irvine, CA.) (Reverse transcriptase uses poly(rA) as template and the annealed oligo(dT) as primer for incorporating the labeled TTP).

The reverse polymerization was started by adding 0.02 µg of recombinant reverse transcriptase protein (ERC BioServices, Rockville, Md.) into 50 µl of coctail. The reaction mixture incubated at 25° C. for 5 minutes.

The reaction was stopped by adding 2 ml of ice cold 20% trichloroacetic acid and the precipitated nucleic acids were filtered onto glass fiber filters, dried with ethanol and their incorporated radioactivity counted in a liquid scintillation counter.

EXAMPLE 2

Inhibitory Effect of Pure Adenosine Diphosphoribosyl Transferase Protein on Human Reverse Transcriptase This example illustrates the inhibitory effect of ADPRT (adenosinediphosphoribose transferase) on human viral reverse transcriptase.

A small amount (300 µg) of ADPRT (0.5 µM) of final concentration was incubated with 100 mM NAD in 3 ml of 25 mM Tris-HCl (pH 7.4), 0.3% Tween 20 at 25° C. for three hours to render the protein auto-poly (ADP-ribosyl)ated, then concentrated to 3 mg/ml. Using generally the reverse transcriptase assay conditions as described in Example 1, the effect of automodified and unmodified ADPRT was monitored.

Results summarized in FIG. 1 show that automodified ADPRT does not inhibit reverse transcription (open circles), while ADPRT inhibits RT in a concentration-dependent manner (closed circles).

EXAMPLE 3

Activation of HIV Reverse Transcriptase by Auto-(ADP-ribosylated) ADPRT

This example illustrates the activation of human immunodeficiency virus reverse transcriptase in vitro cells; in the presence or absence of NAD substrate and its dependence on time.

Incubation coctail was described in Example 1 was used for this procedure with or without presence of NAD (62.5 µM) for 0.05 units of HIV RT.

The mixture was incubated at 25° C. for 5, 10 and 25 minutes, then the recombinant reverse transcriptase was added and the mixture was incubated for additional 5 minutes. The reaction was stopped, as described above, the precipitate was filtered and radioactivity counted.

The results are shown in FIG. 2.

FIG. 2 shows that when ADPRT and its substrate NAD are added for auto (ADP-ribosyl)ation directly into the RT coctail 5, 10 or 25 minutes prior to addition of reverse transcriptase enzyme, one can observe not only an abolition of inhibitory effect but an activation of reverse transcription by HIV RT enzyme.

EXAMPLE 4

Inhibition of HIV Reverse Transcriptase with Inhibitors of poly-ADP-Ribosvlated ADPRT This example illustrates the inhibition of poly-ADP-ribosylation by 6-amino-1,2-benzopyrones and by 5-iodo-6-amino-1,2-benzopyrones in the presence of ADPRT.

Using generally the reverse transcriptase procedure described in Example 1, three groups of samples were prepared. The first group contained the coctail described in the Example 1 containing poly (rA)•oligo $(dT)_{12-18}$ as a template and drugs 6-ABP or 5-I-6-ABP in concentration 1,000 µM and 400 µM, respectively, without the presence of ADPRT.

The second group contained the same ingredients as group 1 but ADPRT at a concentration to 0.5 µM was added to all samples.

The third group contained the same ingredients as group 2 but NAD in a concentration of 62.5 µM was added.

Results are summarized in FIG. 3 wherein the inhibitory effect of 6-ABP and 5-I-6-ABP on poly-ADP-ribosylation is clearly seen.

What is claimed is:

1. A method for inhibiting the poly-ADP-ribosylation of adenosine diphosphoribosyl transferase by administering a pharmaceutically effective amount of 5-iodo-6-amino-1,2-benzopyrones.

2. The method of claim 1 wherein the 5-iodo-6-amino-1,2-benzopyrone is chosen from the group of compounds represented by the formula:

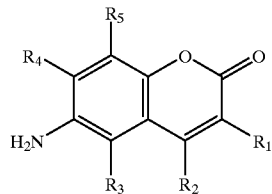

Wherein $R_1$, $R_2$, $R_3$, or $R_4$ are each independently selected from hydrogen, hydroxy, amino, alkyl, alkoxy, cycloalkyl, halo, phenyl or substituted phenyl with alkyl, alkoxy, hydroxy, or halo, or their pharmaceutically active and acceptable salts.

3. The method of claim 2 wherein the compound is 5-iodo-6-amino-1,2-benzopyrone.

4. A method for inhibiting poly-ADP-ribosylation of adenosine diphosphoribosyl transferase in a cell infected by a retrovirus comprising the step of administering an effective amount of 5-iodo-6-amino-1,2-benzopyrones.

5. The method of claim 4 wherein the retrovirus is human immunodeficiency retrovirus.

6. The method of claim 4 wherein the cell is in a mammal.

7. The method of claim 6 wherein said mammal is a human.

* * * * *